(12) United States Patent
Jenneskens et al.

(10) Patent No.: US 11,065,688 B2
(45) Date of Patent: Jul. 20, 2021

(54) NANO-PARTICLES CONTAINING CARBON AND A FERROMAGNETIC METAL OR ALLOY

(71) Applicant: BASF CORPORATION, Florham Park, NJ (US)

(72) Inventors: Leonardus Wijnand Jenneskens, Soest (NL); John Wilhelm Geus, Bilthoven (NL); Bernard Hendrik Reesink, Winterswijk-Kotten (NL); Pieter Hildegardus Berben, Maarn (NL); Jacobus Hoekstra, Utrecht (NL)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 15/433,637

(22) Filed: Feb. 15, 2017

(65) Prior Publication Data

US 2017/0216925 A1 Aug. 3, 2017

Related U.S. Application Data

(63) Continuation of application No. 13/643,896, filed as application No. PCT/NL2011/050296 on Apr. 29, 2011, now abandoned.

(30) Foreign Application Priority Data

Apr. 29, 2010 (EP) ..................... 10161530

(51) Int. Cl.
*B22F 9/24* (2006.01)
*C30B 29/60* (2006.01)
(Continued)

(52) U.S. Cl.
CPC .............. *B22F 9/24* (2013.01); *A61K 49/183* (2013.01); *A61K 49/1863* (2013.01); *B05D 5/00* (2013.01);
(Continued)

(58) Field of Classification Search
CPC .... B22F 9/24; B22F 2201/02; B22F 2201/10; B22F 2201/12; B22F 2201/11; B22F 2201/20; B22F 2201/30; C08K 9/10
(Continued)

(56) References Cited

U.S. PATENT DOCUMENTS

| 4,855,091 A | 8/1989 | Geus et al. |
| 5,456,986 A | 10/1995 | Majetich et al. |

(Continued)

FOREIGN PATENT DOCUMENTS

| CN | 1454851 B | 11/2011 |
| WO | 9946782 | 9/1999 |

(Continued)

OTHER PUBLICATIONS

P. J. F Harris, Chemical physics Letters 293(1998) 53-58 (Year: 1998).*

(Continued)

*Primary Examiner* — Tabassom Tadayyon Eslami
(74) *Attorney, Agent, or Firm* — Lowenstein Sandler LLP

(57) ABSTRACT

The invention relates to nano-particles comprising metallic ferromagnetic nanocrystals combined with either amorphous or graphitic carbon in which or on which chemical groups are present that can dissociate in aqueous solutions. According to the invention there is provided nano-particles comprising metal particles of at least one ferromagnetic metal, which metal particles are at least in part encapsulated by graphitic carbon.

The nano-particles of the invention are prepared by impregnating carbon containing bodies with an aqueous solution of at least one ferromagnetic metal precursor, drying the impregnated bodies, followed by heating the impregnated (Continued)

bodies in an inert and substantially oxygen-free atmosphere, thereby reducing the metal compounds to the corresponding metal or metal alloy.

6 Claims, 3 Drawing Sheets

(51) Int. Cl.
*C30B 7/00* (2006.01)
*B22F 1/02* (2006.01)
*B82Y 30/00* (2011.01)
*B22F 9/26* (2006.01)
*C30B 29/02* (2006.01)
*B22F 1/00* (2006.01)
*B05D 5/00* (2006.01)
*A61K 49/18* (2006.01)
*C23C 16/02* (2006.01)
*C23C 16/26* (2006.01)
*C23C 16/44* (2006.01)
*C23C 16/56* (2006.01)

(52) U.S. Cl.
CPC ............ *B22F 1/0018* (2013.01); *B22F 1/02* (2013.01); *B22F 1/025* (2013.01); *B22F 9/26* (2013.01); *B82Y 30/00* (2013.01); *C23C 16/0227* (2013.01); *C23C 16/26* (2013.01); *C23C 16/4417* (2013.01); *C23C 16/56* (2013.01); *C30B 7/00* (2013.01); *C30B 29/02* (2013.01); *C30B 29/60* (2013.01); *B22F 2009/245* (2013.01); *B22F 2201/10* (2013.01); *B22F 2301/255* (2013.01); *B22F 2301/35* (2013.01); *B22F 2302/40* (2013.01); *B22F 2998/10* (2013.01); *Y10T 428/2991* (2015.01)

(58) Field of Classification Search
USPC ............ 427/249.1, 212, 226, 228; 428/842.4
See application file for complete search history.

(56) References Cited

U.S. PATENT DOCUMENTS

| | | | | |
|---|---|---|---|---|
| 8,709,126 | B1* | 4/2014 | Luhrs | B22F 1/02 75/351 |
| 2006/0116443 | A1 | 6/2006 | Probst et al. | |
| 2006/0137487 | A1 | 6/2006 | McKinnon et al. | |
| 2006/0229466 | A1* | 10/2006 | Arhancet | B01J 21/18 562/531 |
| 2007/0090323 | A1 | 4/2007 | Duguet et al. | |
| 2008/0057001 | A1 | 3/2008 | Sun et al. | |
| 2008/0213189 | A1 | 9/2008 | Lee et al. | |
| 2008/0213367 | A1* | 9/2008 | Sarkar | B82Y 5/00 424/484 |
| 2009/0220767 | A1 | 9/2009 | Schlogl et al. | |
| 2010/0166870 | A1 | 7/2010 | Iyer et al. | |
| 2012/0046162 | A1 | 2/2012 | Hoekstra et al. | |

FOREIGN PATENT DOCUMENTS

| | | | |
|---|---|---|---|
| WO | 03057626 | | 7/2003 |
| WO | 2004107368 | | 12/2004 |
| WO | WO 2006/108683 | * | 10/2006 |
| WO | 2007146426 A2 | | 12/2007 |
| WO | WO 2008/074087 | * | 6/2008 |
| WO | 2009109588 | | 9/2009 |
| WO | 2009135937 | | 11/2009 |
| WO | 2010098668 | | 2/2010 |

OTHER PUBLICATIONS

Russian Office Action issued in Russian Patent Application No. 1211737/71RU, dated Apr. 24, 2015, 5 pgs.
International Search Report in PCT/NL2011/050296, dated Sep. 23, 2011, 3 pages.
Borysiuk, J. et al., "Structure and Magnetic Properties of Carbon Encapsulated Fe Nanoparticles Obtained by Arc Plasma and Combustion Synthesis", Carbon 46 2008 , pp. 1693-1701.
Ha, Byeongchul et al., "Ferromagnetic Properties of Single-Walled Carbon Nanotubes Synthesized by Fe Catalyst Arc Discharge", Physica B 404 2009, pp. 1617-1620.
Harris, P.J.F. et al., "A Simple Technique for the Synthesis of Filled Carbon Nanoparticles", Chemical Physics Letters 293 1998 , pp. 53-58.
Hoekstra, Jacco et al., "Carbon-Supported Base Metal Nanoparticles: Cellulose at Work", ChemSusChem, 2015, pp. 985-989, vol. 8, Issue 6, 5 pages.

* cited by examiner

NANO-PARTICLES CONTAINING CARBON AND A FERROMAGNETIC METAL OR ALLOY

CROSS-REFERENCE TO RELATED APPLICATIONS

This application is a continuation of U.S. patent application Ser. No. 13/643,896, filed Mar. 5, 2013, which is a National Phase entry of PCT/NL2011/050296, filed Apr. 29, 2011, which claims the benefit of priority to European Patent Application No. 10161530.0, filed Apr. 29, 2010, the contents of each being hereby incorporated by reference herein in their entireties.

FIELD

The invention relates to nano-particles comprising metallic ferromagnetic nanocrystals combined with either amorphous or graphitic carbon in which or on which chemical groups are present that can dissociate in aqueous solutions. The field of the invention includes for instance contrast agents for magnetic resonance imaging and for fluorescent imaging, drug delivery, cellular labeling and local thermal therapeutic treatments, such as, hyperthermia.

BACKGROUND

One of the most important applications of ferromagnetic nano-particles is presently as contrast agents for magnetic resonance imaging. The local presence of inhomogeneities in the magnetic field leads to significantly shorter relaxation times $T_1$ and $T_2$ in magnetic resonance. Consequently the local presence of ferromagnetic particles leads to dark spots in magnetic resonance images of protons. A good resolution asks for small ferromagnetic particles of a sufficiently high magnetization.

Generally ferromagnetic oxide particles are employed for magnetic resonance imaging. In atmospheric air the oxidic particles are relatively stable. The most well known ferromagnetic iron oxides are magnetite, $Fe_3O_4$ or $Fe(II)Fe(III)_2O_4$ and maghemite, $\gamma$-$Fe_2O_3$. Combination with other bivalent metal atoms, such as, cobalt or nickel also provides ferromagnetic oxides, e.g., $CoFe_2O_3$ and $NiFe_2O_3$.

Small particles of magnetite are usually produced by mixing of solutions containing Fe(II) and Fe(III) compounds. Depending on the mixing the process can result in small clustered magnetite particles. The ferromagnetic iron oxides produced to be employed with magnetic resonance imaging are known as SPIO, superparamagnetic iron oxide, and very small particles as USPIO, ultra small superparamagnetic iron oxide. Superparamagnetic refers to the fact that the spins in a sufficiently small ferromagnetic particle are not ordered in multidomains. Formation of magnetic multidomains brings about that a magnetic particles does not exhibit a magnetic moment in the absence of an external magnetic field. Sufficiently small ferromagnetic particles do not form multidomains. Small ferromagnetic particles are therefore single-domain particles, which indicates that the moments of the magnetic atoms present in an individual particle are not ordered in different domains, but are oriented in the same direction. Consequently a single-domain particle displays a ferromagnetic moment, also in the absence of an external magnetic field. When the particles are suspended in a liquid without forming clusters, they can rotate freely. Then the orientation of the magnetic moments of the individual particles can assume thermodynamic equilibrium, which will depend upon the magnetic moment of the particles, the strength of the external magnetic field and the thermal energy (temperature). Since in contrast to paramagnetic materials the magnetic moments of ferromagnetic particles involve thousands or millions of atomic magnetic moments, the paramagnetic behavior is denoted superparamagnetism. Magnetic particles that can move more or less freely in a liquid therefore do not exhibit magnetic remanence; without an external magnetic field the magnetization of single-domain particles suspended in a liquid is negligible. When the magnetic anisotropy energy of ferromagnetic particles is of the order of kT, the thermal energy, the orientation of the magnetic moments of the individual particles can also reach thermodynamic equilibrium when the particles cannot bodily rotate.

The magnetic interaction between single-domain particles suspended in a liquid brings about that usually the particles form clusters in which the magnetic moments of the individual particles are thus oriented that again no external magnetic field results. For biomedical applications formation of clusters of magnetic particles is unfavorable.

The SPIO and USPIO particles according to the present state of the art are very small, viz., 4 to 7 nm with the USPIO particles imaged in FIG. 1. Though SPIO and USPIO particles can provide reasonable contrast in magnetic resonance imaging, there are some problems. Commercial materials, such as, Feridex™ and Resovist™, are negatively charged and exhibit a lifetime in blood, which is relatively short (half-time less than 1 hour). Combitran™ involving iron oxide particles of 15 to 30 nm coated with dextran exhibits a much longer lifetime in blood, viz., 24 to 36 hour. The health of living cells is adversely affected by iron species dissolved from the iron oxide particles. The small iron oxide particles are almost invariably strongly clustered. As demonstrated in figure, the ferromagnetic particles are taken up into biological cells as relatively large clusters. The cells do not respond favorably to the relatively large amount of iron oxide thus taken up.

Illustrative for the interest in contrast agents for magnetic resonance imaging are the number of recent patent applications. WO-A-2004/107368 describes magnetic iron oxide particles smaller than 20 nm, the surface of which is modified with amine groups. The isoelectric point is higher than or equal to 10. WO-A-2009/109588 mentions iron oxide particles with two different ligands, the first ligand contains an electrostatically charged group and the second ligand is hydrophilic. WO-A-2009/135937 concerns a linker connected at the first end to a polyethylene imine polymer and at the other end to the nanoparticle core or alternatively to a polyethylene glycol polymer grafted to a polyimine polymer. Also these ferromagnetic oxides are exhibiting problems due to a broad distribution of particle sizes, agglomeration of the individual particles, instability due to reaction or recrystallization to non-ferromagnetic iron oxide and poisonous properties. Particularly problematic is the fact that the ferromagnetic particles are severely clustered.

The ferromagnetic oxide particles are generally clustered and display a relatively low magnetic moment. Small particles that are not clustered of a higher magnetic moment per particle are highly attractive in providing a better contrast at low concentrations. Since the atomic magnetic moments in ferromagnetic metals and alloys are directed in parallel, their magnetization is usually more elevated. However, small metal particles are highly liable to be oxidized by exposure to atmospheric air. Handling small metallic magnetic particles, which are pyrophoric, is therefore difficult. Also the preparation on a sufficiently large scale of small metallic ferromagnetic particles of a narrow distribution of particle sizes is problematic. Finally the relatively high magnetic moment of metallic ferromagnetic particles brings about that clustering of the particles is more difficult to prevent.

Coating the small ferromagnetic metal particles with an inert layer after the preparation is therefore a prerequisite. The present state of the art of metallic ferromagnetic particles therefore includes application of inert layers on the metal particles. U.S. Pat. No. 4,855,091 mentions the production of small nickel, iron or cobalt particles by reduction of suitable precursors applied on a highly porous, ceramic support and subsequently exposing the small particles to a carbon delivering gas flow. The gas flow contains either a hydrocarbon, such as, methane or toluene, and hydrogen or carbon monoxide and hydrogen. The result of the exposure to the above gas flow is the growth of carbon nanofibers out of the metal particles. Generally the metal particles end up at the end of the carbon nanofibers enclosed in graphitic layers or within the carbon nanotubes.

Subsequently the Carnegie Mellon Institute obtained a patent on magnetic metal or metal carbide nanoparticles coated with graphitic layers, U.S. Pat. No. 5,456,986. The procedure was exemplified by the preparation of gadolinium carbide nanocrystallites. The procedure claimed was difficult to scale up and cannot readily provide larger amount of ferromagnetic particles. According to the procedure a hole was drilled in a graphite rod and the hole was filled with the oxide of a ferromagnetic metal or with a paramagnetic rare earth oxide. Subsequently the thus prepared rod was employed in the Kratschmer-Huffmann carbon arc process. The process results in much soot and some magnetic particles, which can be separated by passing the resulting powder through an inhomogeneous magnetic field. The magnetic particles appeared to be not completely coated by graphitic layers and are thus still liable to oxidation.

Ferromagnetic particles produced according to a procedure that is much more easily to scale up have been mentioned in WO-A-99/46782. The data of this patent application are incorporated by reference in their entirety into the present disclosure. The procedure disclosed in this patent involves application of precursors of ferromagnetic metals on highly porous, ceramic supports, such as, alumina or silica. The procedures employed to apply the precursors on the supports are usual to those employed in the production of supported metal catalysts. After reduction of the precursor to the corresponding metal, which is usually performed by keeping the loaded support at high temperatures in a gas flow containing hydrogen, the metal particles are exposed to a carbon delivering gas flow. Decomposition of the carbon delivering gas molecules leads to the growth of one or more graphitic layers on the surface of the metal particles. It is important to note that the graphitic layers are curved at the edges and corners of the metal particles. Growth of carbon nanofibers out of the metal particles is suppressed by operating at a low hydrogen pressure and an elevated temperature. After encapsulation of the metal particles the material is cooled to room temperature and the ceramic support is removed by dissolution. Alumina can be dissolved in, e.g., phosphoric acid or sodium hydroxide, while silica can be dissolved in sodium hydroxide. Reaction of a silica support with the precursor of the ferromagnetic metal has to be prevented, since the resulting metal silicate is not soluble in alkaline solutions. If reaction to a silicate has proceeded, dissolution of the support has to be performed by treatment with hydrofluoric acid. Since hydrofluoric acid is dangerous to handle, treatment with this acid is not attractive with industrial applications.

WO-A-9946782 further discloses that ferromagnetic particles having a permanent magnetic moment are difficult to disperse, since the particles tend to line up in chains. With a preference to line up in circular chains, the remanence is low, whereas the ferromagnetic particles are nevertheless clustered. WO-A-99/46782 therefore proposes to employ small particles of a nickel-iron alloy. Due to the low magnetic anisotropy of specific nickel-iron alloys, such particles assume a single domain arrangement of their atomic magnetic moments only in the presence of an external magnetic field. Though the dispersibility of such nickel-iron particles is excellent, the carcinogenic properties of nickel are less favorable.

Another procedure to produce coated metallic ferromagnetic particles is mentioned in US-A-2008/0057001 now abandoned. This patent application mentions the production of small ferromagnetic particles from the decomposition of the corresponding metal carbonyls at elevated temperatures, 600 to 1200° C. The metal or alloy particles were separated from the gas flow by a chiller. The particles were subsequently brought into a solution of polyethylene glycol or polymeric starch. That oxidation of the metal(s) could not be completely prevented is evident from the saturation magnetization, which was 152.5 emu/g and 60.0 emu/g for iron particles of a mean size of 10 and 26 nm, respectively. The measured saturation magnetizations are considerably lower than the saturation magnetization of bulk iron, which amounts to 222.6 emu/g. It is significant that iron particles coated with carbon also of a mean diameter of 26 nm according to a non-disclosed procedure exhibit a higher saturation magnetization of 119 emu/g. After ultrasonic treatment of the resulting dispersion of coated metal or alloy particles, can be filtered through a filter with 0.1 μm pore size. Images taken with a scanning electron microscope of dispersions of the thus produced particles reveal the cause of the low remanence of dispersions of the metal or alloy particles; as to be expected, the ferromagnetic particles are present in closed loops, thus producing a very low remnant magnetization. It is important to note that the saturation magnetization of the at least partly metallic particles is still significantly higher than that of iron oxide particles, which is about 68 emu/g for Feridex, a commercial iron oxide from Berlex Imaging, a unit of Berlex, Inc.

It is highly interesting that The Board of Trustees of the Leland Stanford Junior University filed a patent application that describes exactly the same procedure as dealt with in the above patent WO-A-99/46782 to produce ferromagnetic particles encapsulated in graphitic layers. The patent application involved is US-A-2008/0213189 now abandoned. This patent application is concentrated on cobalt-iron alloy particles. The saturation magnetization of the FeCo particles was 215 emu/g, which is close to the value of bulk FeCo of 235 emu/g. The functionalization of the carbon coated metal or alloy particles has not been dealt with in WO-A-99/46782 in contrast to US-A-2008/0213189, which claims polar lipids for functionalization. A polar lipid is defined as a molecule with an aliphatic carbon chain with a terminal polar group. More particularly, phospholipids are claimed, which are defined as molecules having an aliphatic carbon chain with a terminal phosphate group. Finally molecules containing alkoxy or thioalkyl groups and alkylamino groups are claimed.

WO-A-03/057626 describes a method of preparing microparticles having a ferromagnetic core encapsulated in a graphitic shell containing hetero atoms. In particular, WO-A-03/057626 describes that the carbon coating of the nanoparticles prepared according to its method contains 7 surface atom % of nitrogen and that such particles are structurally and fundamentally different from nanoparticles whose carbon jacket contains only carbon atoms and is made up of essentially planar plates.

Ha B. et al., *Physica B: Condensed Matter*, 404, 2009, 1617-1620 describes single-walled carbon nanotubes synthesized by Fe catalyst arc discharge, where iron particles are present within the skeins of the carbon nanofibres.

Borysiuk J. et al., *Carbon*, 46, 2008, 1693-1701 describes carbon encapsulated nanoparticles within carbon nanofibres and soot.

Harris P. J. F. et al., *Chemical Physical Letters*, 293(1998) 53-58 describes a method of preparing filled carbon nanoparticles. As disclosed in the micrographs of this article, the filled carbon nanoparticles are produced in conjunction with carbon nanofibres.

US-A-2006/0116443, now abandoned describes metal coated carbon black produced by impregnating carbon black with a metal compound and reducing the metal compound with a reducing agent.

The present invention is directed to improved graphite-coated metallic ferromagnetic particles that are not clustered and produced according to an improved procedure.

The objective of the invention is therefore to provide a nano-particle comprising small ferromagnetic metal particles that are homogeneously distributed, viz. wherein clustering of the ferromagnetic particles is avoided. This was found to be possible if the number of metal particles in the nano-particle is kept below one hundred particles. In order to use the nano-particles for instance in MRI applications, the number of metal particles in each nano-particle should be at least three. Preferably there are less than twenty particles and even more preferably less than ten ferromagnetic particles in each nano-particle. The nano-particle is formed by at least partial encapsulation of the individual ferromagnetic particles by a graphitic layer. If the encapsulation is partial, the surface of the ferromagnetic particles may be further covered by a gold layer. Preferably the ferromagnetic particles are completely covered by a combination of a graphitic carbon and a gold layer.

The objective of the invention is therefore to provide a nano-particle comprising small ferromagnetic metal particles that are homogeneously distributed, viz. wherein clustering of the ferromagnetic particles is avoided. This was found to be possible if the number of metal particles in the nano-particle is kept below one hundred particles. In order to use the nano-particles for instance in MRI applications, the number of metal particles in each nano-particle should be at least three. Preferably there are less than twenty particles and even more preferably less than ten ferromagnetic particles in each nano-particle. The nano-particle is formed by at least partial encapsulation of the individual ferromagnetic particles by a graphitic layer. If the encapsulation is partial, the surface of the ferromagnetic particles may be further covered by a gold layer. Preferably the ferromagnetic particles are completely covered by a combination of a graphitic carbon and a gold layer.

The ferromagnetic metal comprises iron. They may consist entirely, or essentially (e.g. >99 wt. %) of iron. In addition they may contain a small fraction (e.g. 1-5 wt. %) of other metals, in particular other metals that may facilitate the reduction of iron.

Typically the size (largest diameter) of the metal particles is from 1-200 nm, preferably from 10-100 nm. The nano-particles typically have a size (largest diameter) of typically less than 500 nm, preferably 100-200 nm, preferably less than 10 μm and even more preferably less 1 μm in size.

For clinical applications metallic iron particles are preferably employed, since magnetic metals, such as, nickel and cobalt, as well as alloys contained these elements are poisonous. Nevertheless encapsulation in graphitic layer may prevent contact with the poisonous metals with living material. It is therefore essential that all the ferromagnetic particles are completely encapsulated.

Iron oxide and other iron precursors are notoriously difficult to reduce to metallic iron, since the thermodynamic equilibrium calls for a very low water vapor pressure or a very high temperature. With a hydrophilic support, such as, silica or alumina, it is not possible to reduce the water vapor pressure inside the support bodies significantly. The ammonia synthesis catalyst therefore contains no less than 98 wt. % magnetite and only about 1 wt. % alumina together with about 1 wt. % potassium oxide. However, with the usual highly porous oxidic supports, it is not possible to reduce pure iron oxide or iron oxide precursors applied on the surface of the support to metallic iron by reduction with hydrogen. The water vapor pressure inside the support bodies remains too elevated. Very small support bodies cannot be employed, since either the pressure drop of the reducing gas flow is too high or the small loaded support particles will be entrained with the gas flow. That is the reason that the above-mentioned US 2008/0213189 exclusively mentions the preparation of iron-cobalt alloy particles. It is well known that cobalt considerably facilitates the reduction of iron oxide. Another problem with the usual supports, viz., alumina and silica, is that the iron(II) that results from the reduction in the presence of water vapor, is liable to reaction with the support to a spinel $Fe(II)Al_2O_4$ or a silicate. The iron(II) in these highly porous ceramic materials cannot be reduced at temperatures below about 900° C.

SUMMARY

One or more embodiments of the invention are directed to nano-particles comprising 3-100 metal particles of at least one ferromagnetic metal, and a graphitic carbon body, wherein said metal particles are at least in part encapsulated by said graphitic carbon body. In some embodiments, the ferromagnetic metal comprises iron. In one or more embodiments, the ferromagnetic particle further comprises a metal selected from the group of nickel, cobalt, precious metals and combinations thereof. In some embodiments, the ferromagnetic particles are at least partly coated with graphitic carbon and at least partly by a gold layer. In detailed embodiments, the ferromagnetic particles are completely encapsulated by graphitic carbon.

In one or more embodiments, the nano-particles further comprise substituted polynuclear aromatic compounds, which are adsorbed to the surface of said graphitic carbon body. Additional embodiments are directed to processes for the production of a nano-particle comprising a metal-carbon body, wherein said metal-carbon body comprises ferromagnetic metal alloy particles at least partly encapsulated within graphitic carbon. The processes comprise impregnating carbon containing body with an aqueous solution of at least one ferromagnetic metal precursor, drying the impregnated body, followed by heating the impregnated body in an inert and substantially oxygen-free atmosphere at a temperature of 450 to 600° C., thereby reducing the metal compounds to the corresponding metal alloy.

Further embodiments of the invention are directed to processes for the production of a nano-particle comprising a metal-carbon particle, wherein said metal-carbon particle comprises ferromagnetic metal particles at least partly encapsulated within graphitic carbon. The processes comprise impregnating a carbon containing body with an aqueous solution of a metal precursor, drying the impregnated body, followed by heating the impregnated body in an inert and substantially oxygen-free atmosphere at a temperature to above 700° C., thereby reducing the metal compound to the corresponding metal.

In some embodiments of the processes, the ferromagnetic metal is iron. In one or more embodiments, the metal precursor is one or more salts of one or more organic acids selected from the group consisting of citric acid, acetic acid, formic acid, hydroxyl acids and ammonium citrate. In detailed embodiments, carbon containing body is selected from the group consisting of microcrystalline cellulose, colloidal carbon, and mixtures thereof. In specific embodiments, the metal alloy further comprises another metal selected from the group of nickel, cobalt, precious metals, and mixtures thereof. In certain embodiments, the nano-particle comprises amorphous carbon, wherein said nano-particle is treated with an oxidizing agent, removing said amorphous carbon and producing carboxylic acid groups on the graphitic surfaces. In some embodiments, the nano-particle is treated in a flow comprising hydrogen and carbon containing molecules, wherein said nano-particle is completely encapsulated by graphitic carbon. In one or more embodiments, the nano-particle is immersed in an aqueous solution comprising a gold compound, wherein said nano-particle is partly coated in a gold layer.

DETAILED DESCRIPTION

Figure 1:
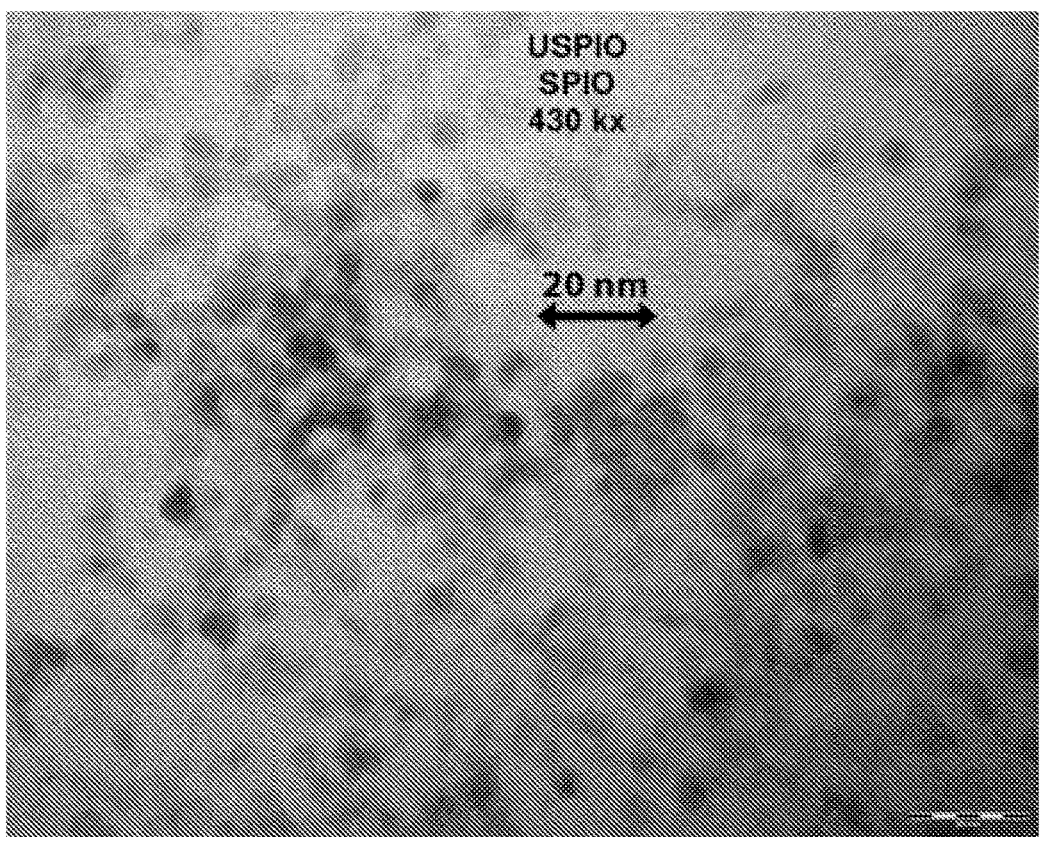
FIG. 1 shows an image of a particle.
Figure 2:
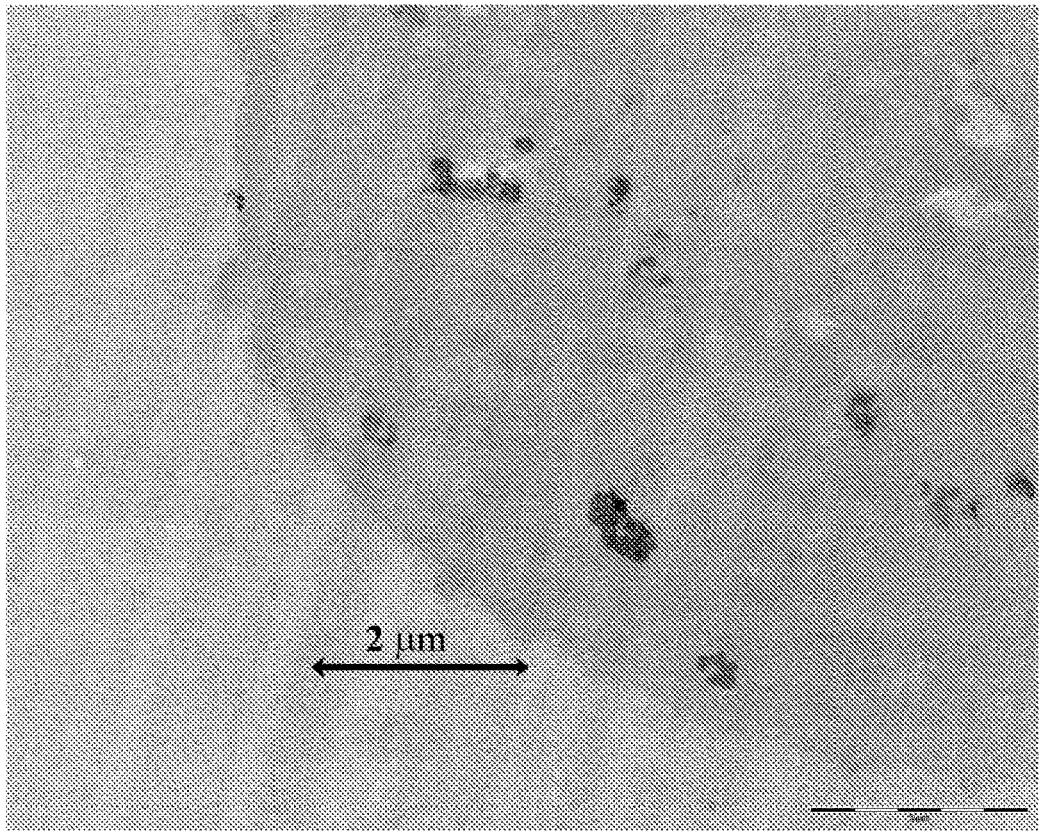
FIG. 2 shows an image of ferromagnetic particles taken up in biologic cells.

The first objective of our invention is therefore the preparation of a nano-particle comprising small ferromagnetic alloy particles containing an iron alloy with other metals that facilitate the reduction of iron.

The next objective is to provide the nano-particle comprising small ferromagnetic alloy particles protection against oxidation by graphitic layers that completely or incompletely cover the surface of the iron particles.

Another objective is to coat the fraction of the surface of the nano-particle comprising ferromagnetic metal particles not covered by graphitic layers with a thin gold layer.

A further objective is the preparation of the nano-particle comprising ferromagnetic particles compatible with biological fluids that do not significantly cluster upon dispersion in an aqueous liquid. This objective of the invention involves therefore application of electrostatically charged groups onto the surface of the graphitic layer encapsulating the ferromagnetic metal particles of the nano-particle.

The procedure described in WO-A-99/46782 and in US 2008/0213189 is not easy to perform on a larger scale. With a fixed bed of ceramic support particles loaded with the precursor of the ferromagnetic metal it is difficult to expose the particles of the loaded ceramic support to a uniform gas composition. Already during the reduction of the metal precursor before the encapsulation the water vapor content of the reducing gas flow varies. With a fixed bed of bodies of the ceramic support the fraction of the bed where the reducing gas flow enters starts to be reduced and the water vapor generated in the reduction flows through the remaining part of the fixed bed. The water vapor delays the reduction of the metal oxide to the corresponding metal or alloy. With iron oxide the water vapor can promote the reaction of iron(II) with the support. The extent of reduction therefore can vary considerably with the position in the bed of the ceramic bodies. Also during the encapsulation by exposure to a carbon delivering gas flow it is difficult to achieve a uniform coating of the iron particles. It is possible that a very rapid growth of carbon nanofibers proceeds within a well reduced fraction of the bed, which consumes virtually completely the carbon delivering molecules. A fixed bed of loaded support bodies, the most obvious configuration, may therefore not be the optimum reactor set up. A thin layer of the support bodies loaded with the small metal particles in a rotating kiln may better deal with the transport problems within the gas phase. However, the support bodies cannot be too small, since the gas flow within the kiln will entrain small support bodies. A fluidized bed of the loaded support bodies is most attractive, but handling a fluidized bed reactor is less easy.

Most problematic is therefore to achieve conditions uniform over a significantly large volume of loaded support bodies, where the growth of carbon nanofibers is not extensive and the metal particles are encapsulated. Usually a significant fraction of the metal particles is not completely encapsulated, which leads to dissolution of the metal particles during the treatment with an acid solution to remove the support. Consequently the production of appropriately coated metal particles is relatively low. A final objective of the invention is therefore to provide a procedure that can be more easily controlled and more easily scaled up than the procedure dealt with in WO-A-99/46782.

Surprisingly it has been found that many of the above objectives can be realized very smoothly for producing a nano-particle according to the present invention by impregnating carbon containing bodies with iron precursors together with small amounts of a metal precursor that facilitates the reduction of iron to metallic iron, drying the impregnated bodies and keeping the bodies in a nitrogen flow, whilst raising the temperature to a level where the bodies decompose to carbon and gaseous material.

Accordingly, another embodiment of the invention is directed to a process for the production of a nano-particle comprising a metal-carbon body, wherein said metal-carbon body comprises ferromagnetic metal alloy particles at least partly encapsulated within graphitic carbon, which process comprises impregnating carbon containing body with an aqueous solution of at least one ferromagnetic metal precursor, drying the impregnated body, followed by heating the impregnated body in an inert and substantially oxygen-free atmosphere, thereby reducing the metal compounds to the corresponding metal alloy.

A preferred carbon body material is microcrystalline cellulose, which is commercially available as spheres of diameters varying from 0.1 to about 0.5 mm. Such spheres are produced for the slow release of drugs. Impregnation of microcrystalline cellulose spheres with a metal precursor can be performed easily. Hydrothermally treated sugar (colloidal carbon) may be employed too as a suitable carbon body. The colloidal carbon may be produced from hydrothermally treated sugar solution at a temperature from 160 to 200° C. Also activated carbon may be used as a suitable carbon body to perform the reduction of iron oxide and to provide the carbon for the encapsulating graphitic layers.

Suitable precursors for the ferromagnetic particles are the salts of the metals. The precursor employed affects the required reduction procedure. Though acceptable results have been obtained with iron(III) nitrate, an explosive reaction with the cellulosic material may proceed. Preferred therefore are salts of organic acids, such as, citric acid, acetic acid or formic acid and even more salts of organic hydroxyl acids. Highly preferred is iron ammonium citrate, a compound that readily decomposes and produces metallic iron at a relatively low temperature when in contact with the decomposed carbon body material.

It has been found that this surprisingly simple procedure readily leads to the nano-particle comprising metal particles encapsulated by graphitic layers, the carbon being provided by the microcrystalline cellulose. Consequently no transport of carbon delivering gas molecules from a gas flow passed through the impregnated bodies to the supported metal particles of the nano-particles is involved. All the metal particles comprised in the nano-particles are subjected to the same conditions, provided the temperature of the microcrystalline cellulosic bodies is fairly uniform. The procedure can also be performed by applying a precursor of the ferromagnetic metal or alloy on activated carbon bodies and keeping the loaded activated carbon bodies in an inert gas at an elevated temperature. Accordingly no hydrogen is required with the procedure according to our invention. The wide explosion limits of hydrogen bring about that the use of hydrogen is not attractive.

The temperature level required to achieve the virtually complete reduction of the metal precursor and the graphitic coating depends first of all of the cellulosic material employed. Usually a temperature of about 450° C. suffices to bring about degradation of the cellulosic material to amorphous carbon. Reduction of the metal precursor depends on the thermodynamic stability of the precursor. Within a temperature range of 450 to about 700° C., iron precursors if present alone are not reduced. To achieve reduction of the iron precursor a component catalytically promoting the reduction is required. Nickel or cobalt can facilitate the reduction of the iron precursor, and we can employ also a precious metal, such as, palladium or platinum, to achieve reduction of the iron precursor. Surprisingly we have observed that a thermal treatment at, e.g., 600° C. leads to metallic alloy particles encapsulated in graphitic layers. Preferably, the temperature of the thermal treatment is from 450 to 600° C.

The content of the metal catalyzing the reduction can be relatively low, e.g., in an amount of less than 5 wt. %, preferably less than 2 wt. %, more preferably from 1-2 wt. % calculated on the basis of the total metal. The nano-particle produced comprises encapsulated alloy particles present within a matrix of amorphous carbon.

The amorphous carbon can be readily removed by oxidation to carbon dioxide. Oxidation with gaseous oxygen can be done by thermal treatment in an oxygen-containing gas flow at a temperature below about 500° C. It has been found that the graphitic carbon in which the metal particles are encapsulated is oxidized by gaseous oxygen only at temperatures above about 500° C., whereas amorphous carbon is oxidized at lower temperatures. The oxidation can also be performed at low temperatures by treatment with a liquid oxidation agent. Preferably the oxidation is executed with nitric acid or a mixture of nitric acid and sulfuric acid.

It is important for the nano-particle produced according to the invention that the oxidation generates oxygen containing groups at defect sites on the surface of the graphitic layers encapsulating the iron (alloy) particles. The oxygen containing groups involve carboxylic acid and phenolic groups. The carboxylic acid groups are ionized beyond pH levels of about 3, at low pH levels a positive charge results from the uptake of a proton on an oxygen atom of the carboxylic acid group. The thus introduced electrostatic charge on the surface of the coated iron particles prevents clustering of the nano-particles. Since the nano-particles comprising small metal particles resulting from the oxidation treatment remain in the liquid and can readily be separated from the liquid by an inhomogeneous magnetic field, a treatment at low temperatures in a liquid phase is preferred according to our invention.

It has, surprisingly, been observed that polynuclear aromatic compounds containing one or more substituents capable of dissociating in aqueous solutions are irreversibly adsorbed on graphitic carbon from aqueous solutions. According to an alternative embodiment of our invention therefore such polyaromatic compounds are adsorbed onto the surface of the graphitic layers encapsulating the alloy particles of the nano-particle. The electrostatic charge on the graphite is due to the dissociated chemical groups substituted into the polyaromatic compound which stabilizes the dispersion of the particles. Preferably compounds derived from pyrene are employed to be adsorbed on the graphitic surfaces.

The nano-particle comprises ferromagnetic alloy particles containing a high content of metallic iron encapsulated in graphitic layers well dispersed in an aqueous liquid is the first embodiment of our invention. The iron content of the nano-particle can vary between 70 and 98 wt. % of the metallic phase; and is preferably above 90 wt. %.

As to be expected from the thermodynamics the reduction of not promoted, and, hence, pure iron oxide to metallic iron is much more difficult. Nevertheless pure metallic iron particles are to be preferred for clinical applications since no poisonous metal are present. When the procedure according to our invention is utilized, a temperature of at least about 700° C. is required to provide metallic iron particles, which are strongly ferromagnetic. It is surprising that thermal treatment for a relatively short period of time at a temperature that is relatively low for the reduction of an iron precursor leads to metallic iron with iron precursor applied in either microcrystalline cellulose bodies, bodies prepared from colloidal carbon produced by hydrothermal treatment of sugar, or activated carbon bodies.

Accordingly, a further embodiment of the invention is directed to a process for the production of a nano-particle comprising a metal-carbon particle, wherein said metal-carbon particle comprises ferromagnetic metal particles at least partly encapsulated within graphitic carbon, which process comprises impregnating a carbon containing body with an aqueous solution of a metal precursor, drying the impregnated body, followed by heating the impregnated body in an inert and substantially oxygen-free atmosphere at a temperature to above 700° C., thereby reducing the metal compound to the corresponding metal.

We have found that inhomogeneous distribution of the impregnation solution may lead to occasional large iron particles at the external edges of the carbon bodies, as well as much more numerous very small metallic iron particles.

Inhomogenities of this sort can be prevented by thoroughly stirring the mixture during reaction.

The size of the small iron particles can be controlled by the loading of the cellulosic material with the iron precursor. A higher loading leads to larger iron particles. Iron particles of about 3 nm can be readily obtained.

Treatment of the nano-particle with hydrochloric acid and measuring the volume of the evolved hydrogen indicates that many iron particles are incompletely encapsulated in contrast to iron particles produced at lower temperatures. It may be attractive to employ nano-particles comprising small iron particles not completely encapsulated, since it may be that biological cells can deal better with slowly dissolving iron particles. In view of the high magnetic moment of metallic iron nano-particles comprising a small number of iron particles is sufficient to indicate the location of a cell in a MRI experiment.

To achieve complete encapsulation of the nano-particle treatment in a flow comprising hydrogen and carbon containing molecules, such as aromatic compounds, including benzene and toluene, CO, $CH_4$, $C_2H_4$ or other gases such as the lower alkanes, alkylenes, alcohols, alkyns, and the like, at about 500° C. is sufficient. Preferably the nano-particle treated by such a flow does not comprise nickel, since this can result in the undesired production of carbon nanofibres. More preferably, the nano-particle treated by such a flow has only iron as the metal in the nano-particle, since this produces surprisingly good results, in particular because nanofibre generation is completely suppressed.

The nano-particle comprising bodies containing iron particles and carbon may then be ground. The large iron particles may then be readily removed in an inhomogeneous magnetic field of a low strength. The large iron particles are also not coated with graphitic layers. After complete encapsulation of the small iron particles, the large iron particles may also be removed by treatment with a mineral acid, e.g., hydrochloric or sulfuric acid.

Since many biological interesting groups can be attached to gold surfaces, e.g., by reaction of the surface with a mercaptane (thiol), sulfide or disulfide group, a nano-particle comprising metallic iron particles having a fraction of the surface coated with a gold layer are also interesting. Accordingly, a nano-particle comprising metallic iron particles and is partly covered with graphitic layers and partly covered with a gold layer is another embodiment of our invention. A gold layer can be readily applied on the iron surface of the nano-particle by immersion of the nano-particle comprising iron particles in a solution of a gold compound, such as, gold chloride. The iron atoms at the surface of the nano-particle are exchanged for gold atoms.

It has surprisingly observed that treatment of microcrystalline cellulosic materials loaded with precursors of metals capable of forming metal carbides at temperatures above about 700° C. leads to conversion of the amorphous carbon into graphitic ribbons. With nano-particles comprising iron and iron-nickel particles the conversion can be almost complete. Graphitic carbon exhibits attractive properties to adsorb specific molecules or to chemically attach specific molecules. A nano-particle comprising graphitic carbon containing small ferromagnetic iron particles either completely or incompletely encapsulated by graphitic layers, is therefore another embodiment of our invention.

Nano-particles containing encapsulated metallic iron particles and graphitic carbon can easily be ground to small bodies. By magnetic separation the nano-particles containing ferromagnetic particles can be separated from the clusters containing only carbonaceous material. It is highly important that the magnetic interaction between nano-particles coated with graphitic layers and attached to graphitic carbon is relatively small, since the nano-particles cannot approach each other closely. Since the magnetic force varies with the square of the distance between the nano-particles, a larger inter-particle distance leads to a much lower magnetic interaction. Preferably the nano-particles comprising graphitic bodies contain less than one hundred, preferably less than twenty and even more preferably less than ten ferromagnetic particles. Since the magnetic moments of the ferromagnetic particles in a graphitic body of the nano-particle assume an orientation in which they neutralize each other completely or partly, it is important that the number of ferromagnetic particles per graphitic body of the nano-particle is at least three. Since the external magnetic moment is greatly reduced with more than three ferromagnetic particles within a graphitic carbon body of the nano-particle according to the invention, the dispersibility of such nano-particles is significantly improved.

The abovementioned alternative embodiment of the invention concerned application of suitably substituted molecules containing polyaromatic groups on the surface of nano-particles comprising ferromagnetic particles coated by graphitic layers. When the coated ferromagnetic particles of the nano-particles are attached to graphitic carbon due to conversion of the initially amorphous carbon to graphitic ribbons, the adsorption of molecules containing polyaromatic groups is appreciably higher. Substitution of suitable groups on the polyaromatic molecules involves first of all polar groups, such as, sulfonic acid or carboxylic acid groups as well as amines. Secondly, substituents imposing water solubility, such as oligo(ethylene glycols), hybrid oligo(ethylene glycol/propylene glycol), can also be employed. It is surprising that polyaromatic molecules substituted with polar groups adsorb irreversibly from aqueous solutions on the surface of graphitic carbon.

A further embodiment of the invention therefore concerns pure iron particles coated by graphitic layers present in graphitic bodies on the graphitic surface of which appropriately substituted polyaromatic compounds have been adsorbed. In particular, the nano-particles according to our invention may be suspended in an aqueous solution, wherein the aqueous solution comprises substituted polynuclear aromatic compounds which adsorb onto the surface of the graphitic carbon. The polynuclear aromatic compounds can be substituted with chemical groups which dissociate in aqueous solution, thus stabilizing the suspended nano-particles in the aqueous solution.

A preferred polyaromatic group according to our invention is pyrene and the molecules preferably adsorbed onto the graphitic surfaces of the nano-particles according to our invention comprises substituted pyrenes.

The adsorbed functionalized polyaromatic groups can be used as a scaffold for the covalent attachment of linker and/or spacer molecules enabling the coupling of other probe and target molecules and/or assemblies responsive to external physical, chemical and/or biological stimuli.

The nano-particle according to our invention also comprises pure encapsulated iron particles within a graphitic matrix in which the graphitic surfaces are functionalized according to the state of the art for the surfaces of carbon nanofibers. Many publications deals with the functionalization of the surfaces of carbon nanofibers. As an instance, we refer to D. Tasis, N. Tagmatarchis, A. Bianco and M. Prato Chem. Rev. (2006) 106 pages 1105-1136. It is highly important that the material that results from the treatment at temperatures above 700° C. contains graphitic material to which the state of the art of functionalization of surfaces of carbon nanotubes can be applied.

The nano-particle according to our invention, which comprises a metal-carbon body, more in particular ferromagnetic metal or metal alloy particles encapsulated within graphitic carbon, is suitable to be used for contrast agents for magnetic resonance imaging and for fluorescent imaging, drug delivery, cellular labelling and local thermal therapeutic treatments, such as, hyperthermia.

Example 1

Commercially available Micro Crystalline Cellulose (MCC) spheres (Cellets, neutral pellets of Syntapharm GmbH, Miilheim an der Ruhr, Germany), of a size range of 100-200 μm were loaded by immersing the spheres into an aqueous solution of iron ammonium citrate. The spheres were left in the solution for 24 h during which the solution was occasionally stirred. Next, the impregnated spheres were separated from the liquid using a Büchner funnel with glass filter. The separated spheres were dried at room temperature in vacuo to constant weight.

Figure 3:
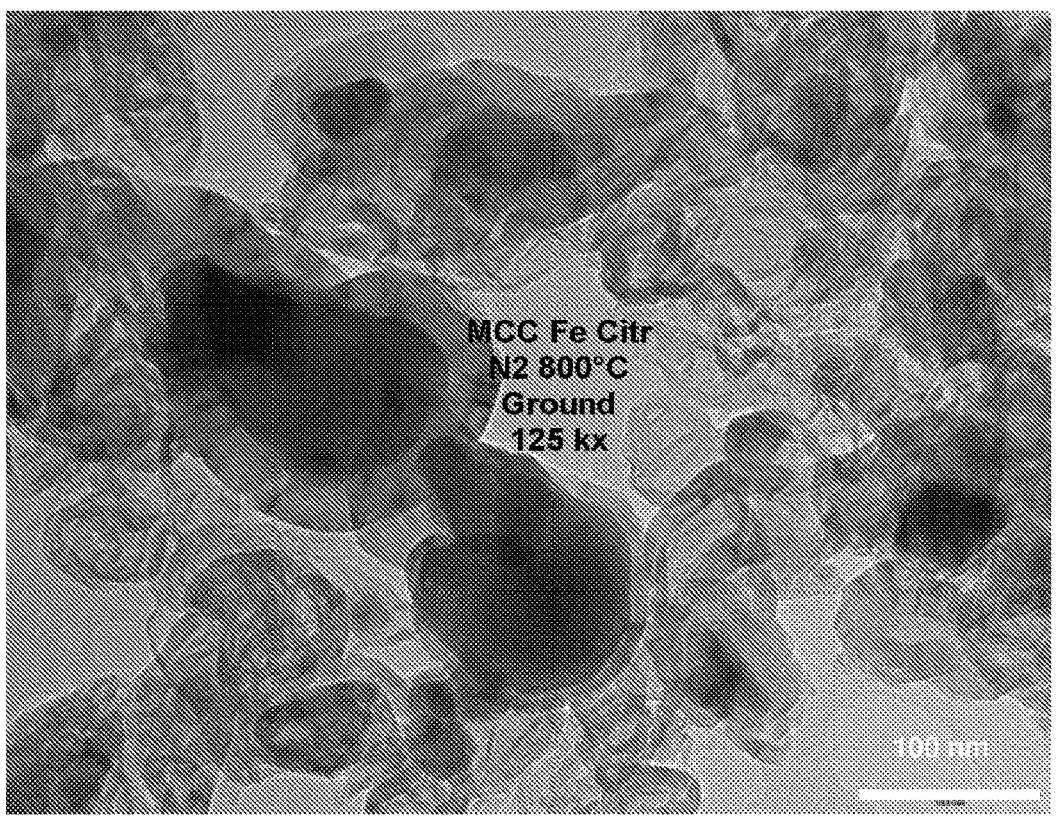
FIG. 3 shows a TEM image of a ground sample in accordance with one or more embodiments of the invention.

Subsequently, the impregnated spheres were pyrolyzed by thermal treatment in an inert nitrogen gas flow in a fluidized bed reactor. The heating rate was 5° C./min and the samples were kept for 3 h at 800° C. This resulted in nano-particles comprising metal-carbon containing bodies with ferromagnetic properties with a size of approximately 70 μm. The reduced iron particles were homogeneously dispersed throughout the metal carbon containing body of the nano-particles. The nano-particles comprising metallic iron particles were partly encapsulated in a graphitic envelope and were in the size range of 10-100 nm as can be inferred from the Transmission-Electron-Micrograph image of a ground sample, as seen in FIG. 3. The amount of iron in the described sample was 8.28 wt %, as measured with ICP-MS. Upon subsequent treatment with concentrated hydrochloric acid, hydrogen gas evolution was observed, indicating that not all the iron particles were completely encapsulated. From the amount of hydrogen gas evolved, the amount of iron that dissolved, was calculated as approx. 20% of the original iron content.

Example 2

Commercially available Micro Crystalline Cellulose (MCC) spheres (Cellets, neutral pellets of Syntapharm GmbH, Miilheim an der Ruhr, Germany), of a size range of 100-200 μm were loaded by immersing the spheres into an aqueous solution of iron ammonium citrate. The spheres were left in the solution for 24 h during which the solution was occasionally stirred. Next, the impregnated spheres were separated from the liquid using a Büchner funnel with glass filter. The separated spheres were dried at room temperature in vacuo to constant weight. Subsequently, the impregnated spheres were pyrolyzed by thermal treatment in an inert nitrogen gas flow in a fluidized bed reactor. The heating rate was 5° C./min and the samples were kept for 3 h at 800° C. A subsequent treatment with toluene in a hydrogen-nitrogen (50/50) gas flow led to nano-particles comprising metal-carbon containing bodies with ferromagnetic properties with a size of approximately 70 μm.

Figure 4:
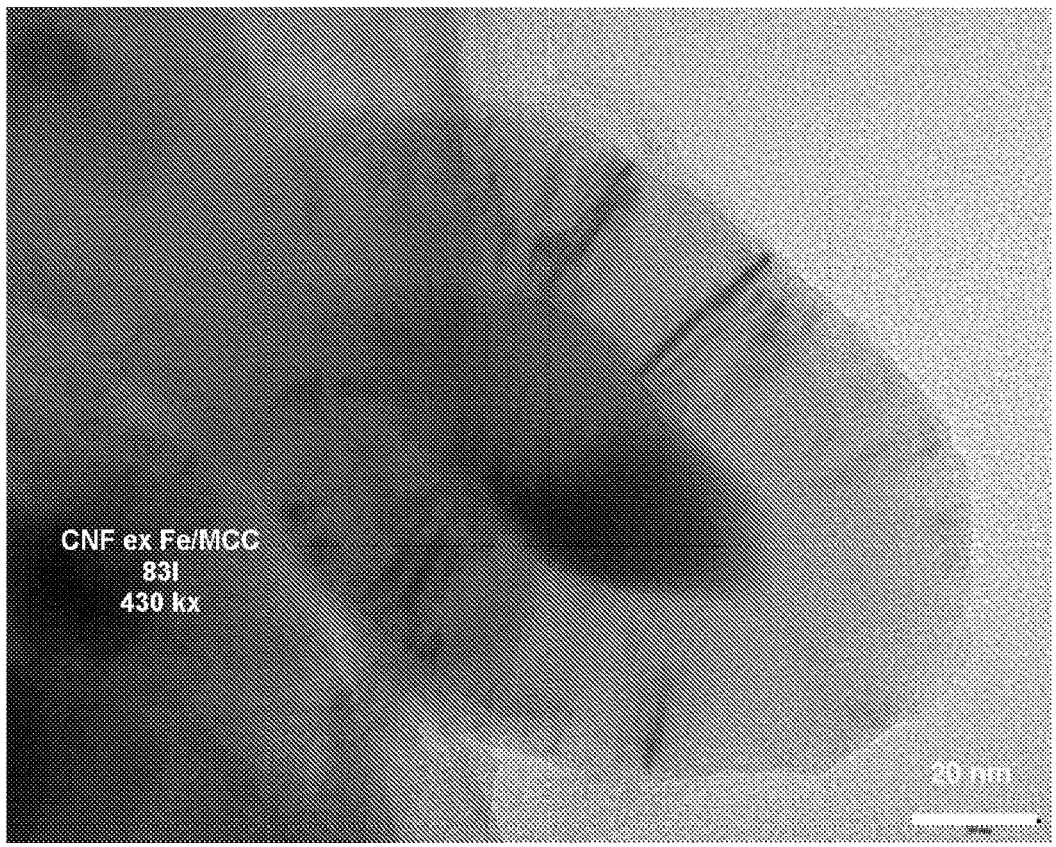
FIG. 4 shows a TEM image of an encapsulated iron particle in accordance with one or more embodiments of the invention.

The reduced iron particles were homogeneously dispersed throughout the metal carbon-bodies of the nano-particles. Upon subsequent treatment with concentrated hydrochloric acid, no hydrogen gas evolution was observed, indicating that all the iron particles were completely encapsulated in the nano-particles. FIG. 4 shows a Transmission Electron Micrograph of an encapsulated iron particle obtained by grinding the original sample.

Example 3

Figure 5:
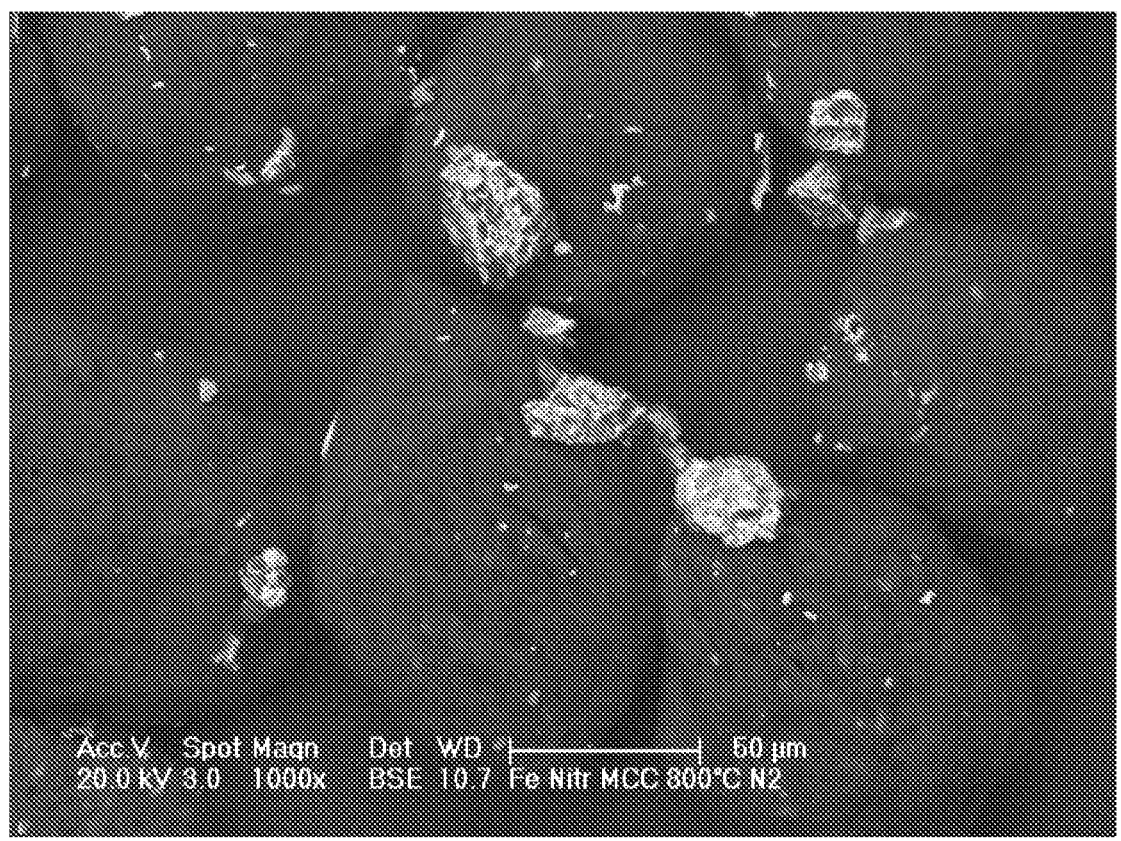
FIG. 5 shows a Back Scattered Electron Micrograph of a particle in accordance with one or more embodiments of the invention.

Commercially available Micro Crystalline Cellulose (MCC) spheres (Cellets, neutral pellets of Syntapharm GmbH, Miilheim an der Ruhr, Germany), of a size range of 100-200 μm were loaded by immersing the spheres into an aqueous solution of iron nitrate. The spheres were left in the solution for 24 h during which the solution was occasionally stirred. Next, the impregnated spheres were separated from the liquid using a Büchner funnel with glass filter. The separated spheres were dried at room temperature in vacuo to constant weight. Subsequently, the impregnated spheres were pyrolyzed by thermal treatment in a stationary inert nitrogen gas flow in a tube furnace reactor. The heating rate was 5° C./min and the samples were kept for 3 h at 800° C. This resulted in nano-particles comprising metal-carbon containing bodies with ferromagnetic properties with a size of approximately 70 μm. Some large iron particles are formed at the external edge of the carbon bodies of the nano-particles (see FIG. 5, Back Scattered Electron Micrograph, indicating the heavy element, iron at a relatively high intensity) besides much more numerous very small metallic iron particles.

Example 4

The nano-particles comprising graphite-encapsulated iron particles were brought in an aqueous solution of N,N,N-trimethyl-2-oxo-2-(pyren-1-yl)ethanaminium bromide (formula (I) below), with a pyrene-carrying ammonium ion synthesized according to N. Nakashima, Y. Tomonari and H. Murakami, "Water-Soluble Single-Walled Carbon Nanotubes via Noncovalent Sidewall-Functionalization" Chem. Lett. 31, P. 638-639, 2002. This probe is known to have a strong interaction with the graphitic surfaces of carbon nanotubes. The pyrene-carrying ammonium-ion adsorbed irreversibly onto the graphitic surfaces of the nano-particles. The depletion of the pyrene-carrying ammonium-ion from the solution was followed by UV-Vis-spectroscopy. After an ultrasonic treatment a stable homogeneous dispersion of the nano-particles comprising graphite encapsulated iron particles was obtained.

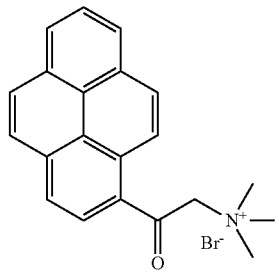

(I)

Example 5

The nano-particles comprising graphite-encapsulated iron particles were brought in an aqueous solution N-2-(2-(2-methoxyethoxy)ethoxy)ethyl)pyrene-1-carboxamide (formula (II) below). The pyrene-carrying oligo-ethylene-glycol tail irreversibly adsorbed onto the graphitic surfaces. The depletion of the pyrene-carrying ammonium-ion from the solution was followed by UV-Vis-spectroscopy. After an ultrasonic treatment a stable homogeneous dispersion of the nano-particles comprising graphite encapsulated iron particles was obtained.

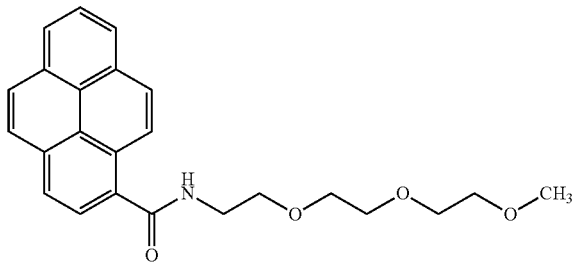

(II)

Example 6

The nano-particles graphite-encapsulated iron particles were brought in an aqueous solution of N-(2-(2-(2-methoxyethoxy)ethoxy)ethyl)-N,N-dimethyl-2-oxo-2-(pyren-1-yl)ethanaminium bromide (formula (III) below). The pyrene with both a hydrophilic and an electrostatic group adsorbs irreversibly to the graphitic surfaces. The depletion of the pyrene-carrying ammonium-ion from the solution was followed by UV-Vis-spectroscopy. After an ultrasonic treatment a stable homogeneous dispersion of the nano-particles comprising graphite encapsulated iron particles was obtained.

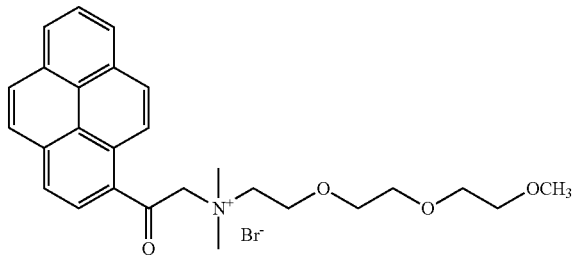

(III)

What is claimed is:

1. A process for the production of a nano-particle comprising a metal-carbon particle, wherein the metal-carbon particle comprises ferromagnetic metal particles at least partly encapsulated within graphitic carbon, wherein the process comprises:

impregnating a carbon containing body with an aqueous solution of a metal precursor;

drying the impregnated body; and after drying the impregnated body, heating the impregnated body in a gas atmosphere at a temperature of above 700° C. to reduce a metal compound in the impregnated body to the ferromagnetic metal particles and to at least partly encapsulate the ferromagnetic metal particles within the graphitic carbon, wherein the gas atmosphere consists of inert gas.

2. The process according to claim 1, wherein the ferromagnetic metal is iron.

3. The process according to claim 1, wherein the metal precursor is one or more salts of one or more organic acids selected from the group consisting of citric acid, acetic acid, formic acid, hydroxyl acids and ammonium citrate.

4. The process according to claim 1, wherein the carbon containing body is selected from the group consisting of microcrystalline cellulose, colloidal carbon, activated carbon bodies and mixtures thereof.

5. The process according to claim 1, wherein the nano-particle comprises amorphous carbon, wherein the nano-particle is treated with an oxidizing agent, removing the amorphous carbon and producing carboxylic acid groups on the graphitic surfaces.

6. The process according to claim 1, wherein the nano-particle is further treated in a flow comprising hydrogen and carbon containing molecules, wherein the nano-particle is completely encapsulated by graphitic carbon.

* * * * *